US007829016B2

(12) United States Patent
Deal et al.

(10) Patent No.: US 7,829,016 B2
(45) Date of Patent: Nov. 9, 2010

(54) C-BAND DISINFECTOR (76) Inventors: Jeffery L. Deal, 1570 Spinnaker La., Charleston, SC (US) 29407; Philip J. Ufkes, 1085 Deleisseline Blvd., Mount Pleasant, SC (US) 29464; David R. Deal, 4942 W. Price Rd., Sewanee, GA (US) 30024

( * ) Notice: Subject to any disclaimer, the term of this patent is extended or adjusted under 35 U.S.C. 154(b) by 582 days.

(21) Appl. No.: 11/705,279

(22) Filed: Feb. 12, 2007

(65) Prior Publication Data
US 2008/0075629 A1    Mar. 27, 2008

Related U.S. Application Data (63) Continuation of application No. 10/373,270, filed on Feb. 24, 2003, now Pat. No. 7,175,806.

(60) Provisional application No. 60/364,720, filed on Mar. 15, 2002.

(51) Int. Cl.
*A61L 2/10* (2006.01)
(52) U.S. Cl. .............................. 422/24; 422/3
(58) Field of Classification Search ....................... None
See application file for complete search history.

(56) References Cited

U.S. PATENT DOCUMENTS

| 3,683,638 | A |   | 8/1972  | Devon |
| 3,936,186 | A |   | 2/1976  | Boland et al. |
| 4,366,125 | A | * | 12/1982 | Kodera et al. ............... 422/295 |
| 5,288,547 | A |   | 2/1994  | Elmes et al. |
| 5,527,704 | A | * | 6/1996  | Wolf et al. ............... 435/283.1 |
| 5,597,597 | A |   | 1/1997  | Newman |
| 5,637,877 | A |   | 6/1997  | Sinofsky |
| 6,028,315 | A | * | 2/2000  | Bailey et al. ........... 250/455.11 |
| 6,433,343 | B1 |  | 8/2002  | Cimino et al. |
| 6,461,569 | B1 |  | 10/2002 | Boudreaux |
| 6,767,453 | B2 |  | 7/2004  | Lifschitz |
| 6,911,177 | B2 |  | 6/2005  | Deal |

FOREIGN PATENT DOCUMENTS

| DE | 2929805   | 1/1981  |
| GB | 2364622   | 1/2002  |
| JP | 11009546  | 1/1999  |
| WO | WO 9953966 | 10/1999 |

* cited by examiner

*Primary Examiner*—Elizabeth L McKane
(74) *Attorney, Agent, or Firm*—B. Craig Killough (57) ABSTRACT A C-Band Disinfector disinfects objects placed within the interior of the device by subjecting the objects to emissions of UV-C radiation. Multiple UV-C sensors measure UV-C radiation dosage to the objects and control the period of operation of the device, terminating the emission of UV-C radiation only after all of the UV-C radiation sensors have received a minimum predetermined dosage.

35 Claims, 5 Drawing Sheets

C-BAND DISINFECTOR

CROSS-REFERENCE TO RELATED APPLICATION

The contents of Provisional Application Ser. No. 60/364,720 filed Mar. 15, 2002 and U.S. Utility application Ser. No. 10/373,270 filed Feb. 24, 2003, now U.S. Pat. No. 7,175,806, on which the present application is based and benefit claimed under 35 U.S.C. §119(e), are herein incorporated by reference.

BACKGROUND OF THE INVENTION

The nature of bacteria acquired in the health care setting differs significantly from bacteria found in a community setting, primarily in their resistance to antibiotic therapy. Abundant evidence exists, however, that the hospital environment itself contributes to the problem by harboring virulent strains of bacteria, fungi, and viruses, and that many disinfection methods commonly used are ineffective and may actually spread contaminants. These contaminants are present on objects, and in particular, instruments, such as endoscopes. These instruments must be decontaminated between uses.

Multiple needs exist to provide disinfection or decontamination of objects that are not suitable for treatment by an autoclave or similar methods. These include, but are not limited to, the exterior of mail, fruits and certain other food items, medical instruments, food handling devices, and other objects that are contaminated with biological hazards.

Examples of such objects are flexible and rigid endoscopes. Endoscopy is a common procedure in modern medical practices. Endoscopes are used to examine and surgically manipulate the sinus cavities, upper and lower gastrointestinal tracts, lung fields, larynx, and intra-abdominal spaces. These endoscopes may have interior channels or conduits that are difficult to reach and disinfect. Relatively straightforward methods exist to disinfect endoscopes that have simple architecture, such as those that do not have interior channels, although the working life of the endoscopes is lessened by chemical degeneration of the seals. An ongoing problem has been the reliable disinfection of endoscopes that have interior channels. These channels are used to inject liquid irrigants, suction, and to pass flexible instruments such as biopsy forceps. These types of interior chambers have represented a challenge to infection control efforts.

Ultraviolet irradiation, particularly in the C bandwidth (2537 Angstroms), when given in adequate doses is lethal to all known pathogens. Ultraviolet irradiation in the C bandwidth (UV-C) is being used to disinfect water supplies, air duct systems, and recently entire patient care areas. The use of UV-C to disinfect endoscopes has not been accomplished to date primarily because of the unavailability of methods of delivering UV-C radiation to interior channels, the unavailability of methods of measuring cumulative dosing that assure adequate decontamination, and the unavailability of methods of measuring UV-C levels that are delivered to the object to be decontaminated.

Microbes are uniquely vulnerable to the effects of light at wavelengths at or near 2537 Angstroms, due to the resonance of this wavelength with molecular structures. For the purposes of this document, the term UV-C is used for a wavelength of light being utilized for its germicidal properties, this wavelength being in the region of 2537 Angstroms.

Recent advances in fiber-optic technology have resulted in fiber optics that efficiently transmit UV-C, thus providing an opportunity to overcome the difficulty of disinfecting interior chambers, channels and conduits of devices and instruments, including endoscopes. Fiber-optic cables have been commercially developed to transmit carrier waves of ultraviolet light, and to allow remote measuring of ultraviolet levels. Also, the method of measuring an accumulating total energy delivered has recently been developed relative to area disinfecting methods, and effective dose ranges have been established.

The United States Food and Drug Administration and the United States Center For Disease Control and Prevention define disinfection as the use of a chemical procedure that eliminates virtually all recognized pathogenic microorganisms but not necessarily all microbial forms (e.g., bacterial endospores) on inanimate objects. There are three levels of disinfection: high, intermediate, and low. High-level disinfection kills all organisms, except high levels of bacterial spores, and is effected with a chemical germicide cleared for marketing as a sterilant by the Food and Drug Administration. Intermediate-level disinfection kills mycobacteria, most viruses, and bacteria with a chemical germicide registered as a "tuberculocide" by the Environmental Protection Agency (EPA). Low-level disinfection kills some viruses and bacteria with a chemical germicide registered as a hospital disinfectant by the EPA. For the purposes of this document, "disinfection" includes all three of these levels, although disinfection is not achieved solely by chemical means by the process described herein.

SUMMARY OF THE INVENTION

The present invention is a C-Band Disinfector that disinfects objects placed within the device by subjecting the objects to closed-loop emissions of UV-C radiation. UV-C sensors measure reflected UV-C radiation from the device's interior surfaces and from the objects themselves. The UV-C sensor information is used to determine when a prescribed dose of UV-C radiation has been applied. In an additional embodiment, UV-C radiation is transmitted by fiber-optic cable to a particular area of an object to be disinfected, and that area continues to be exposed with UV-C radiation until the prescribed dose is applied, which may be measured by a sensor. After the prescribed dose is applied, the fiber-optic cable is moved to a new area of the object, and the UV-C disinfection process continues until all areas of the object have been disinfected by exposure to the prescribed dose of the UV-C radiation.

DESCRIPTION OF THE PREFERRED EMBODIMENT

The C-Band Disinfector provides decontamination of medical instruments and other objects, with little or no risk of harm to the instruments or objects during the process. The device uses medium pressure mercury bulbs, or other bulbs that produce ultraviolet light in the UV-C range, housed in a vertical chamber to irradiate the exterior of an object, such as medical instrument.

Figure 1:
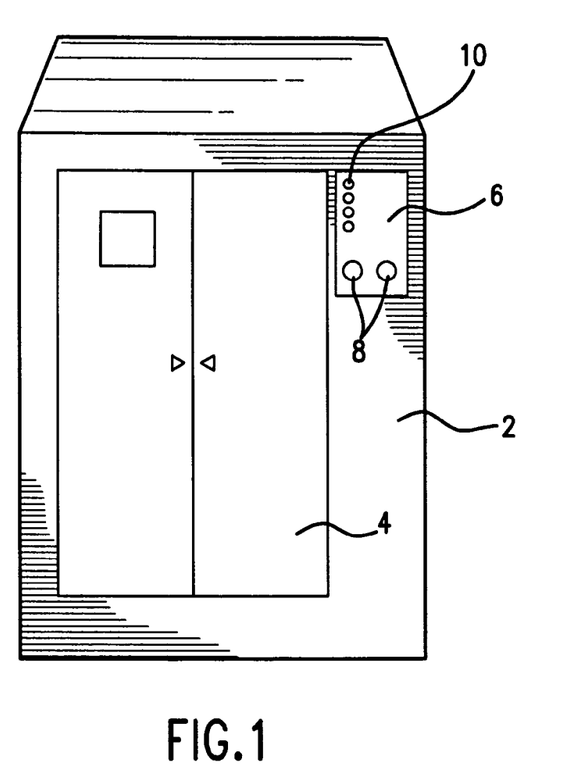
FIG. 1 is a front elevation of the C-Band Disinfector.

FIG. 1 shows a housing for an embodiment of the device. The housing 2 is preferred to be formed of a metal that is easy to clean, such as stainless steel or powder coated steel. All interior surfaces are preferred to be highly UV-C reflective and configured so as to maximize the dispersion of the reflected UV-C radiation within the sterilization chamber. The reflectivity of the interior surfaces of the housing should not be less than 80%. The device may be capable of floor or wall mounting, according to the user's preference, and according to the overall size of the device.

The interior is constructed so that dispersion of UV-C radiant flux energy throughout the sterilization chamber is uniform, with both "hot spots" and "shadows" minimized. In this way, the object to be disinfected is treated on all surfaces as uniformly as possible by reflected, if not direct, UV-C radiation.

In the embodiment as shown as FIG. 1, the device has doors 4 that allow access to the interior of the device, and an external control panel 6. The external control panel may have on-off (start-stop) switches 8 and indicator lights 10 that show the status of the process (in-process, complete, error).

Figure 2:
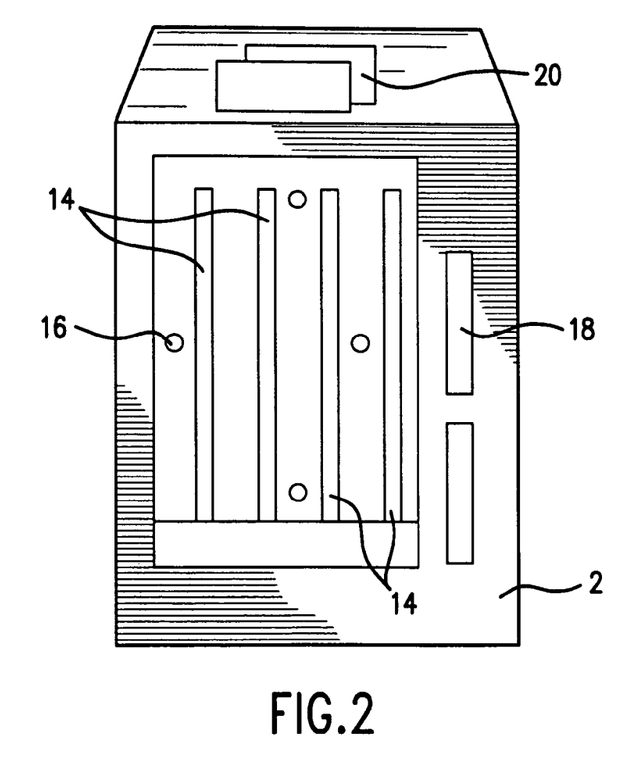
FIG. 2 is a front elevation of the C-Band Disinfector, showing the internal components of the device.

Internally, the device has a plurality of UV-C lamps 14. The UV-C lamps form a bulb array, with the number and location of the bulbs dependent upon the size of the device. The bulbs may be placed on any or all interior surfaces. The bulbs may be protected by fused-quartz glass with high UV-C transmittance.

The device has a plurality of UV-C sensors 16 positioned therein. Multiple sensors may be present on any or all-interior surfaces. In the preferred embodiment, the sensors are located so as to only measure reflected UV-C radiation.

Figure 6:
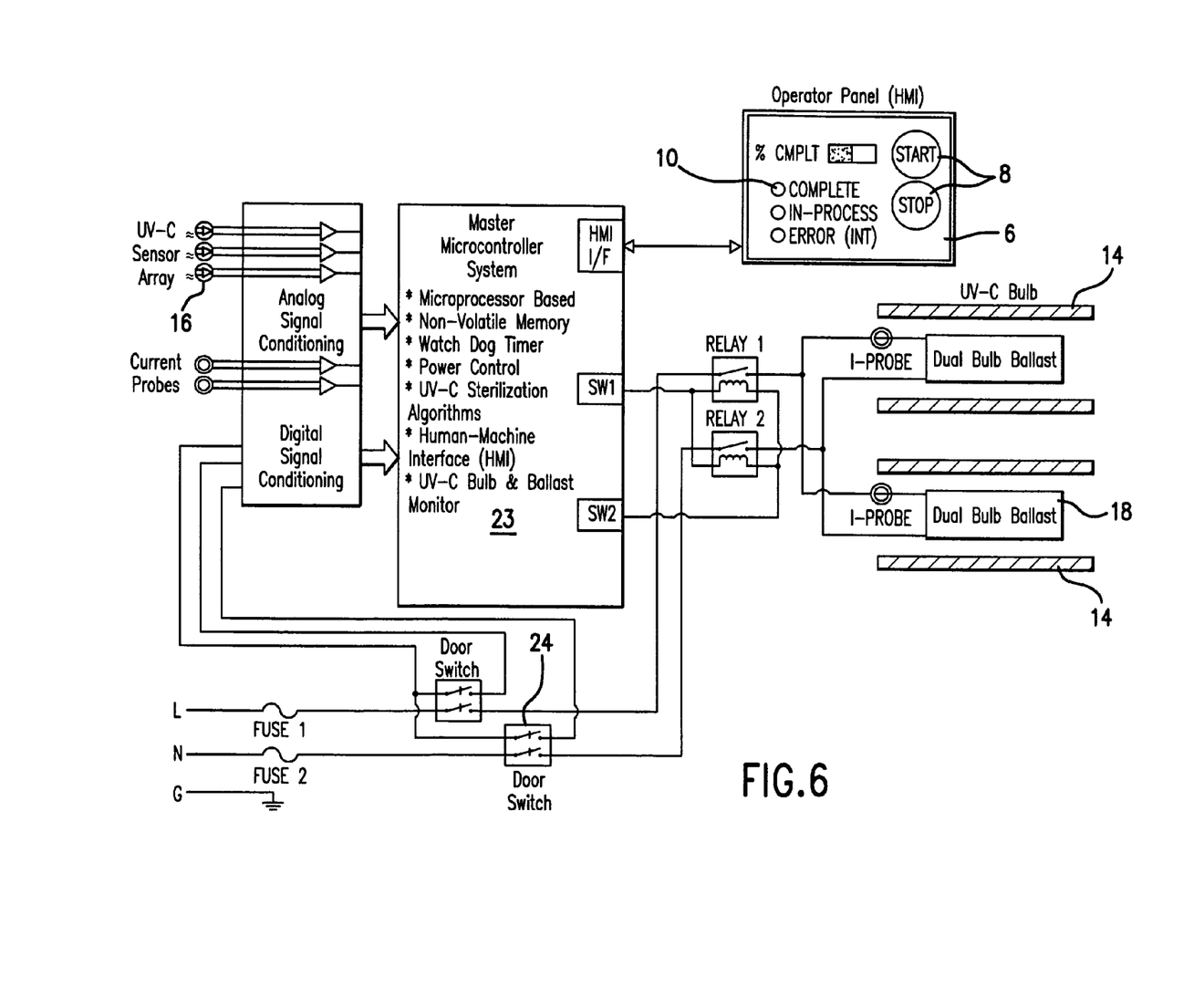
FIG. 6 is a schematic of an embodiment of the C-Band disinfector.
Figure 7:
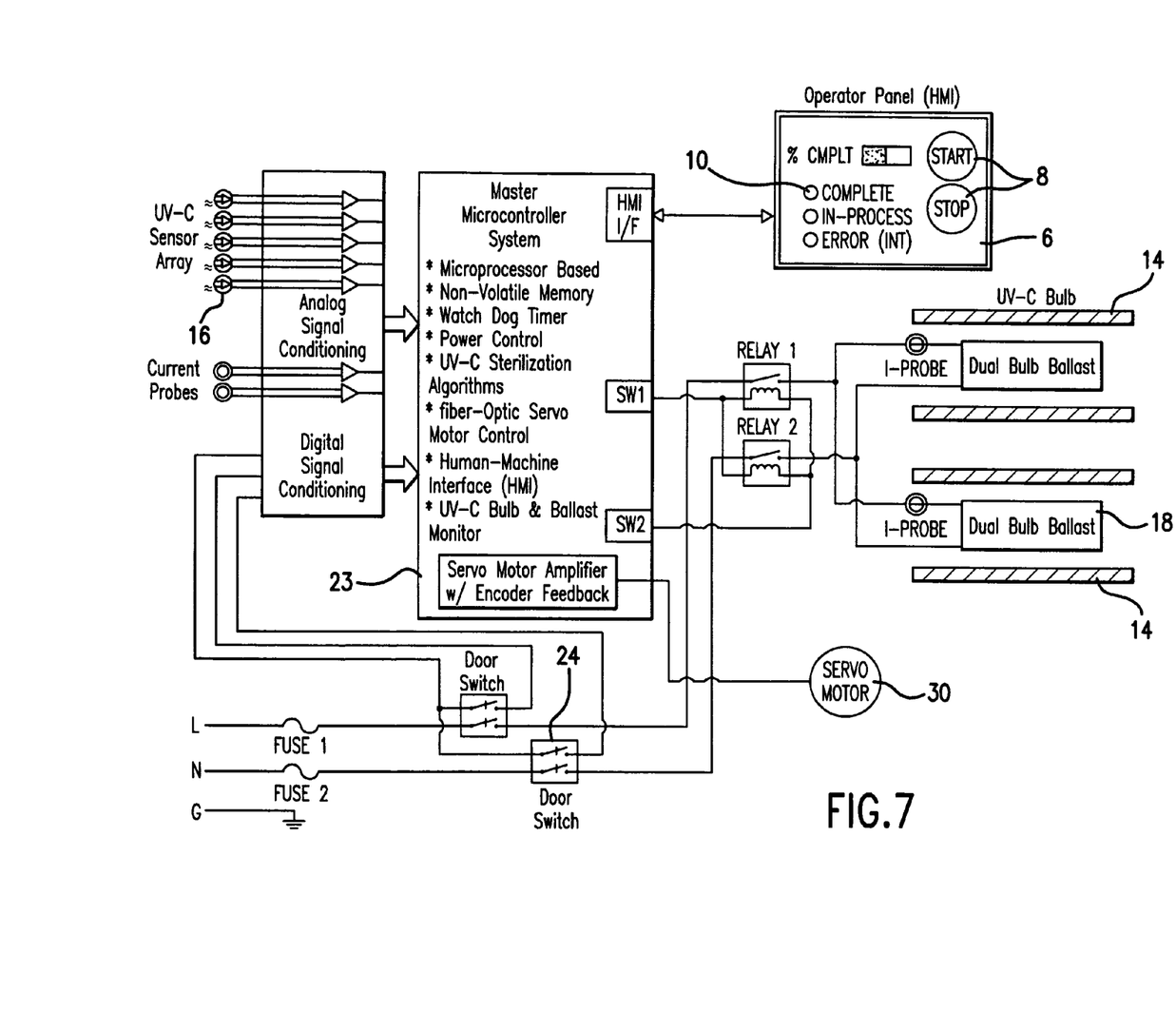
FIG. 7 is a schematic of an additional embodiment of the C-Band disinfector.
Figure 8:
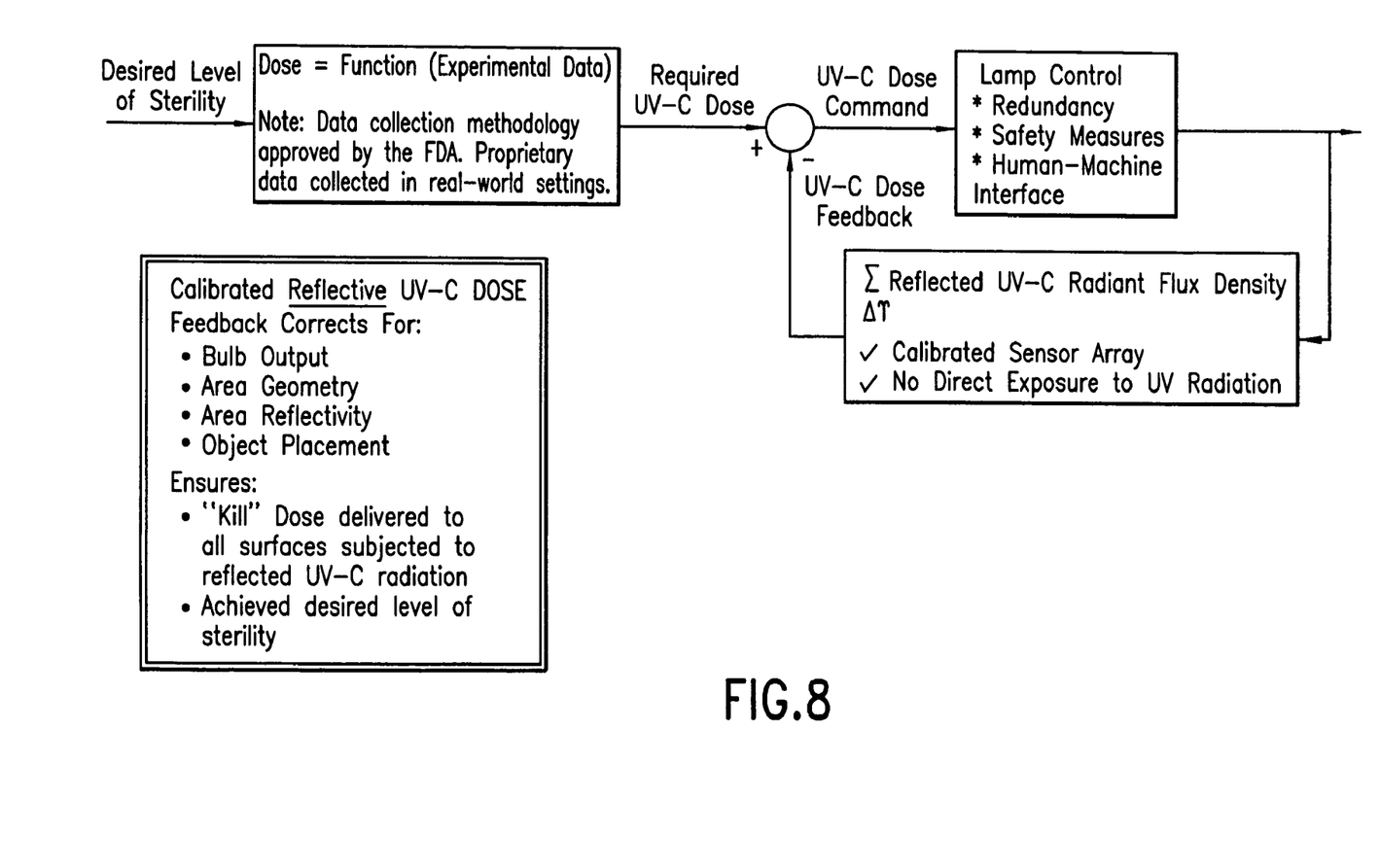
FIG. 8 is a block diagram.

The microcontroller system 20 reads the UV-C sensors. Sterilization control algorithms use the measured UV-C radiant flux density to determine when all surfaces of the object have been exposed to a desired UV-C dosage (FIG. 6; FIG. 7; FIG. 8). Ballasts 18 are also provided within the device.

In use, endoscopes 22 are placed into the interior of the device. Endoscopes, such as rigid endoscopes, may not have interior channels. Rigid endoscopes that do not have interior channels are demonstrated in FIGS. 3 and 4. These endoscopes are placed into the device, and the doors are closed. The device is actuated by means of an appropriate switch, and UV-C radiation is emitted from the bulb array. Direct and reflected UV-C radiation strikes all exterior surfaces of the endoscopes, and disinfects the endoscopes.

Prior to actuating the device, a desired level of disinfection or UV-C dosage level may be selected. FIG. 6. Each of the sensors receives reflected UV-C radiation, and the cumulative UV-C radiation received by each sensor is transmitted to, and measured by, the microcontroller 23. When the required reflected dosage of UV-C has been received by all of the sensors, the microcontroller terminates power to all of the UV-C bulbs. By placing sensors at multiple locations within the device, it can be assured that all parts of the device have received, at a minimum, the required dosage. While certain sensors may receive more than the required dosage, the device continues to operate until each of the sensors has achieved at least the minimum programmed dosage. Control algorithms, based on the principle that electromagnetic energy in free air is dissipated in proportion to one divided by the distance from the radiation source squared, insure that the minimum required UV-C dose is transmitted to all external surfaces of the object.

Other features of the device include a door switch 24 that keeps the cabinet from being opened while the device is emitting UV-C radiation. Further, the device is preferred to have a timer algorithm that will override the operation of the device, so that it does not continue to operate for an excessive period of time, even if the minimum dosage is not apparently received by each of the sensors. For example, if a sensor is blocked, or if a sensor is defective, the algorithm will shut the device down so that the device does not run indefinitely. In the event that the microcontroller shuts the device down, an error message is displayed on the control panel.

Other features may include monitoring the current delivered to the light source so as to determine when bulb replacement is required and calibration curves stored within each of the UV-C sensors. Current flowing to the ballast(s) may be monitored, and an hour meter is provided for each of the bulbs. After the passage of a preset number of hours, the user is notified that the bulb should be replaced. Also, an algorithm monitors the current, and insures that the current is within certain limits. If not, either a bulb has burned out, or a ballast has failed.

A serial EEPROM is provided on the sensor printed circuit board. The sensor is calibrated to a traceable source, and this calibration curve is stored within the EEPROM. When a new sensor is installed, the control system reads the new calibration curve from the sensor. This feature facilitates subsequent re-calibration and replacement of sensors.

Figure 3:
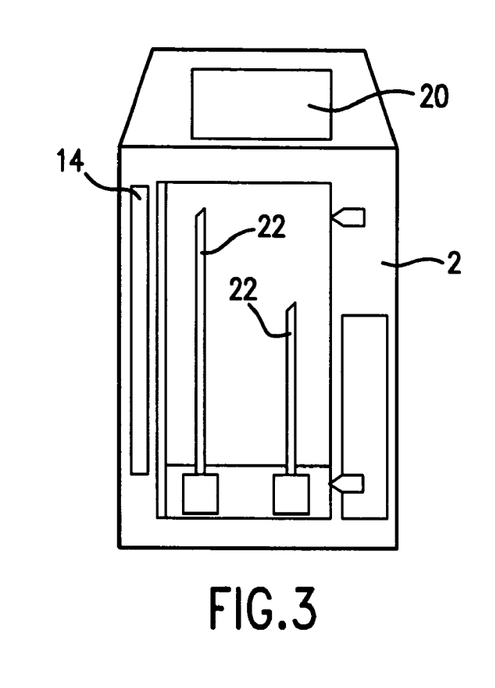
FIG. 3 is a front elevation of an embodiment of the C-Band Disinfector, showing the device in use.

The embodiment shown in FIG. 3, and in the schematic of FIG. 6, is useful for devices that do not have interior channels. For devices that have interior channels, and due to their structure, will not receive reflected or direct UV-C radiation, an additional embodiment or feature of the device must be provided. In particular, many flexible endoscopes have an internal channel or conduit that is enclosed, and will not receive reflected or direct UV-C radiation.

Figures 4, 5:
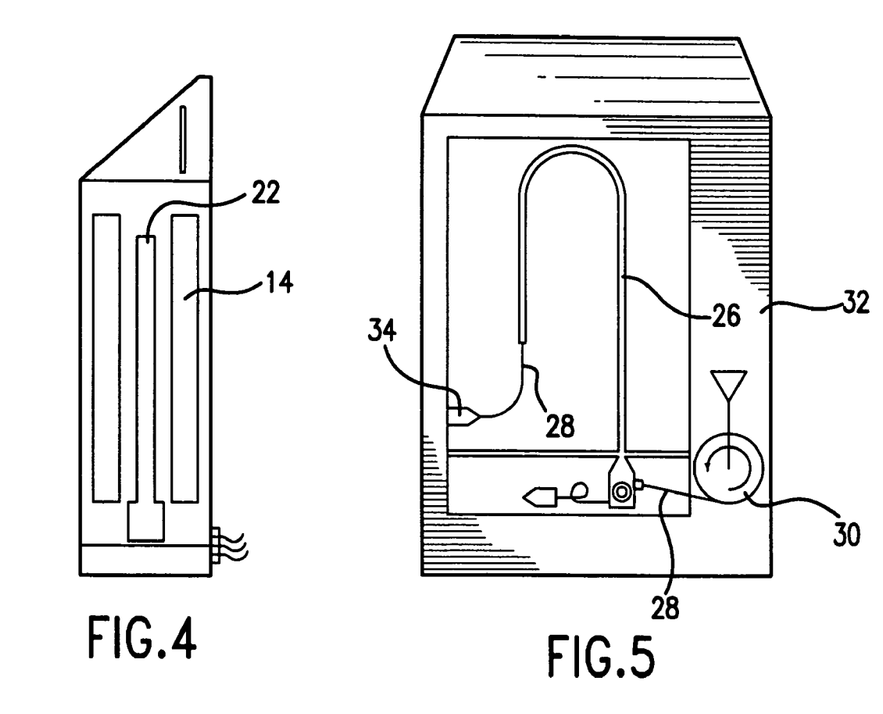
FIG. 4 is a side elevation of an embodiment of the C-Band Disinfector, showing the device in use.
FIG. 5 is an additional embodiment of the C-Band disinfector, showing the device in use.

For endoscopes 26 or other objects with channels the embodiment of the device shown in FIG. 5 and FIG. 7 may be used. After placement of the endoscope into the cabinet 32, and prior to activation of the UV-C lamps and the UV-C source 36 for the fiber-optic cable, the user inserts a quartz laminate fiber-optic cable 28, through interior chambers of the endoscope 26, and into a sensor 34 that is tuned to measure the intensity of light transmitted through the cable. This sensor is read by microcontroller system, which controls the rate of withdrawal of the fiber-optic cable from the endoscope channel with a velocity-controlled withdrawal device 30.

The chamber 32 in which the scopes are hung is constructed of, or coated with, a material that reflects UV-C. As described above, UV-C sensors inside the chamber measure the cumulative dose, and the sensors send data to a microprocessor that activates and deactivates the UV-C bulbs, to assure adequate dosing to the exterior of the endoscopes. The bulbs illuminating the interior of the chamber and the exterior of the endoscopes are shut down when a disinfecting dose of UV-C has been measured within the chamber. Simultaneous to the activation of the bulbs, a Deuterium light source 36, or similar UV-C light source tuned to deliver UV-C to the fiber optic cable is activated. After an appropriate delay to allow a steady-state output, the microprocessor calculates the rate of withdraw of the cable needed to allow for adequate dosing of the channel being treated. The controlled withdrawal device begins to extract the fiber optic cable at the calculated rate. The rate of withdrawal and thus the total exposure of the channel to UV-C are adjusted according to the intensity of the light measured coming from the fiber-optic device. This accounts for variations in lamp intensity over extended use as well as individual variations in light transmission of the fiber-optic cable. As the cable is withdrawn it emits lethal doses of UV-C to the interior chamber.

The controlled withdrawal device may comprise a geared velocity controlled motor connected to a rubberized soft pulley system. It is designed to pull the fiber optic cable from the disinfection chamber at a reproducible and controlled speed without damaging the cables. The cable is fed into a coiling chamber located above the light source. The rate of withdrawal of the cable is controlled by the microprocessor and is dependent on the intensity of UV-C measured by the cable output sensor.

In an alternative embodiment of the device, a bundle of fiber optics that is part of the cable transmits reflected light to a sensor that communicates the information to the microprocessor. The microprocessor controls the rate of withdrawal based upon reflected light received by the sensor during the withdrawal process, rather than basing the withdrawal rate on the light emitted. The bundle of fibers transmits UV-C energy to the channel, while a separate bundle of fibers, that are part of the same fiber-optic cable, transmits reflected light back to a sensor, for transmission of the information to the microprocessor. In this embodiment, the rate of withdrawal is controlled according to the dosage of reflected light received by the microprocessor at any given position of the fiber optic cable relative to the interior of the endoscope.

The device thus disinfects the exterior and interior of the endoscope or other object to be treated. Unlike prior wet disinfection devices, this device produces no hazardous wastes or byproducts, does not chemically degrade the endoscope seals, and is estimated to accomplish the task in less time.

The device may be used to disinfect other objects having crevices or channels. The fiber optic or similar material may be used to direct the UV-C radiation into crevices and channels and destroy pathogens that lurk there.

The endoscopes to be disinfected should be washed of obvious contaminates prior to use with clean water and one or more appropriate cleaning agents. Endoscopes, or other objects to be disinfected, that do not have channels may be treated without use of the fiber-optic withdrawal embodiment.

Some objects are sensitive to degradation by UV-C radiation. These objects, or the relevant portion thereof, may be treated or coated with a UV blocking agent for protection from UV-C radiation. Specifically, some fiber-optic cables degrade when exposed to UV-C, and UV-C blocking is desirable. UV protection, as is commonly placed on optical lenses, such as sunglasses or reading glasses, eliminates the problem of UV-C degradation.

Data is available regarding the levels of UV-C necessary to disinfect against a wide range of organisms including *bacillus anthrax*, staphylococcal species, pseudamonal species, and *e. coli* species. Previously published data related solely to levels used to kill bacterial species in wet solution. The inventors have found that wet bacteria require less UV-C energy to deactivate than do bacteria in a dry state such as are found on contaminated objects. This data is critical to the use of UV-C to achieve the goals of disinfection or decontamination.

What is claimed is:

1. A process of disinfecting an object, comprising the steps of:
    placing an object to be disinfected in a housing, said housing comprising:
    a plurality of UV-C radiation sources in an interior thereof;
    a plurality of UV-C sensors in an interior thereof, wherein said sensors are positioned within said housing to receive and measure UV-C radiation dosages received at multiple spaced apart locations within said interior of said housing, so as to indicate cumulative radiation dosages received at substantially all surfaces of said object to be disinfected; and
    UV-C reflective interior surfaces;
    wherein said object is spaced apart from said plurality of UV-C radiation sources and said plurality of UV-C sensors;
    causing said plurality of UV-C radiation sources to emit UV-C radiation, and directing the emission of UV-C radiation from said plurality of UV-C radiation sources toward said object and toward said UV-C reflective interior surfaces, wherein said UV-C reflective interior surfaces reflect said UV-C radiation and substantially all surfaces of said object receive UV-C radiation;
    measuring a cumulative dosage of UV-C radiation received by each of plurality of said UV-C sensors wherein said plurality of UV-C sensors receive substantially only reflected UV-C radiation;
    terminating the emission of UV-C radiation from said plurality of UV-C radiation sources upon each of said plurality of UV-C sensors receiving a required minimum cumulative dosage of UV-C radiation.

2. A process of disinfecting an object as described in claim 1, wherein said object has an interior channel therein, and said process further comprises the step of progressively exposing said interior channel to UV-C radiation emitted from a fiber-optic material that receives and transmits UV-C radiation from an additional UV-C radiation source, by progressively transporting said fiber-optic material through said interior channel.

3. A process of disinfecting an object as described in claim 2, further comprising a velocity controlled motor, wherein said velocity controlled motor progressively withdraws said fiber-optic material from said interior channel of said object.

4. A process of disinfecting an object as described in claim 2, wherein a rate of progression of said fiber-optic material though said channel of said object is responsive to a level of UV-C radiation received by a sensor that receives and measures UV-C radiation emitted by said fiber-optic material.

5. A process of disinfecting an object as described in claim 1, wherein said object has an interior channel therein, and said process further comprises the steps of:
    progressively exposing said interior channel to UV-C radiation emitted from a fiber-optic material that receives and transmits UV-C radiation from an additional UV-C radiation source, by progressively transporting said fiber-optic material through said interior channel;
    detecting UV-C radiation emitted from said fiber-optic material;
    measuring a cumulative dosage of UV-C radiation detected; and
    terminating an emission of UV-C radiation from said fiber-optic material after a desired cumulative dosage of UV-C radiation is measured.

6. A process of disinfecting an object as described in claim 5, further comprising a velocity controlled motor, wherein said velocity controlled motor progressively withdraws said fiber-optic material from said interior channel of said object.

7. A process of disinfecting an object as described in claim 5, wherein a rate of progression of said fiber-optic material though said channel of said object is responsive to a level of UV-C radiation received by a sensor that receives and measures UV-C radiation emitted by said fiber-optic material.

8. A process of disinfecting an object as described in claim 1, wherein substantially an entire interior of said housing is UV-C reflective.

9. A process of disinfecting an object as described in claim 8, wherein the reflectivity of said interior of said housing is at least 80%.

10. A process of disinfecting an object as described in claim 1, wherein said object is a medical instrument.

11. A process of disinfecting an object as described in claim 10, further comprising the steps of:
   determining a predetermined minimum reference level of UV-C radiation for the medical instrument to be disinfected; and
   terminating the emission of UV-C radiation after determining that the required predetermined minimum reference level of UV-C radiation has been received by each of said sensors.

12. A process of disinfecting an object as described in claim 10, further comprising the step of wetting said medical instrument prior to causing said plurality of UV-C radiation sources to emit UV-C radiation.

13. A process of disinfecting an object as described in claim 10, wherein said medical instrument is an endoscope.

14. A process of disinfecting an object as described in claim 1, further comprising the step of applying UV-C blocking material to areas of said object that are subject to UV-C degradation prior to causing said plurality of UV-C radiation sources to emit UV-C radiation.

15. A process of disinfecting an object as described in claim 1, further comprising the step of wetting said object prior to causing said plurality of UV-C radiation sources to emit UV-C radiation.

16. A process of disinfecting an object as described in claim 1, wherein termination of said UV-C radiation is controlled by a microprocessor that reads the plurality of UV-C sensors and terminates emission of UV-C radiation from the plurality of UV-C sources according to an algorithm that determines when surfaces of the object to be disinfected have received the required minimum dosage of UV-C radiation.

17. A process of disinfecting an object as described in claim 1, wherein said UV-C reflective interior surfaces are arranged to reflect UV-C radiation at said object so that the UV-C radiation received by said object is substantially uniform.

18. A process of disinfecting an object as described in claim 1, further comprising the steps of:
   determining a predetermined minimum reference level of UV-C radiation for the object to be disinfected according to the specific pathogen or pathogens to be treated; and
   terminating the emission of UV-C radiation after determining that the required predetermined minimum reference level of UV-C radiation has been received by each of said sensors.

19. A process of disinfecting an object, comprising the steps of:
   placing an object to be disinfected in a housing, said housing comprising:
      a plurality of UV-C radiation sources in an interior thereof;
      a plurality of UV-C sensors in an interior thereof, wherein said sensors are positioned within said housing to receive and measure UV-C radiation dosages received at multiple spaced apart locations within said interior of said housing, so as to indicate cumulative radiation dosages received at substantially all surfaces of said object to be disinfected; and
      UV-C reflective interior surfaces;
   wherein said object is spaced apart from said plurality of UV-C radiation sources and said plurality of UV-C sensors;
   applying UV-C blocking material to areas of said object that are subject to UV-C degradation prior to causing said plurality of UV-C radiation sources to emit UV-C radiation;
   causing said plurality of UV-C radiation sources to emit UV-C radiation, and directing the emission of UV-C radiation from said plurality of UV-C radiation sources toward said object and toward said UV-C reflective interior surfaces, wherein said UV-C reflective interior surfaces reflect said UV-C radiation and substantially all surfaces of said object receive UV-C radiation;
   measuring a cumulative dosage of UV-C radiation received by each of plurality of said UV-C sensors;
   terminating the emission of UV-C radiation from said plurality of UV-C radiation sources upon each of said plurality of UV-C sensors receiving a required minimum cumulative dosage of UV-C radiation.

20. A process of disinfecting an object as described in claim 19, wherein said object has an interior channel therein, and said process further comprises the step of progressively exposing said interior channel to UV-C radiation emitted from a fiber-optic material that receives and transmits UV-C radiation from an additional UV-C radiation source, by progressively transporting said fiber-optic material through said interior channel.

21. A process of disinfecting an object as described in claim 20, further comprising a velocity controlled motor, wherein said velocity controlled motor progressively withdraws said fiber-optic material from said interior channel of said object.

22. A process of disinfecting an object as described in claim 20, wherein a rate of progression of said fiber-optic material though said channel of said object is responsive to a level of UV-C radiation received by a sensor that receives and measures UV-C radiation emitted by said fiber-optic material.

23. A process of disinfecting an object as described in claim 19, wherein said object has an interior channel therein, and said process further comprises the steps of:
   progressively exposing said interior channel to UV-C radiation emitted from a fiber-optic material that receives and transmits UV-C radiation from an additional UV-C radiation source, by progressively transporting said fiber-optic material through said interior channel;
   detecting UV-C radiation emitted from said fiber-optic material;
   measuring a cumulative dosage of UV-C radiation detected; and
   terminating an emission of UV-C radiation from said fiber-optic material after a desired cumulative dosage of UV-C radiation is measured.

24. A process of disinfecting an object as described in claim 23, further comprising a velocity controlled motor, wherein said velocity controlled motor progressively withdraws said fiber-optic material from said interior channel of said object.

25. A process of disinfecting an object as described in claim 23, wherein a rate of progression of said fiber-optic material though said channel of said object is responsive to a level of UV-C radiation received by a sensor that receives and measures UV-C radiation emitted by said fiber-optic material.

26. A process of disinfecting an object as described in claim 19, wherein substantially an entire interior of said housing is UV-C reflective.

27. A process of disinfecting an object as described in claim 26, wherein the reflectivity of said interior of said housing is at least 80%.

28. A process of disinfecting an object as described in claim 19, wherein said object is a medical instrument.

29. A process of disinfecting an object as described in claim 28, further comprising the steps of:
   determining a predetermined minimum reference level of UV-C radiation for the medical instrument to be disinfected; and
   terminating the emission of UV-C radiation after determining that the required predetermined minimum reference level of UV-C radiation has been received by each of said sensors.

30. A process of disinfecting an object as described in claim 28, further comprising the step of wetting said medical instrument prior to causing said plurality of UV-C radiation sources to emit UV-C radiation.

31. A process of disinfecting an object as described in claim 28, wherein said medical instrument is an endoscope.

32. A process of disinfecting an object as described in claim 19, further comprising the step of wetting said object prior to causing said plurality of UV-C radiation sources to emit UV-C radiation.

33. A process of disinfecting an object as described in claim 19, wherein termination of said UV-C radiation is controlled by a microprocessor that reads the plurality of UV-C sensors and terminates emission of UV-C radiation from the plurality of UV-C sources according to an algorithm that determines when surfaces of the object to be disinfected have received the required minimum dosage of UV-C radiation.

34. A process of disinfecting an object as described in claim 19, wherein said UV-C reflective interior surfaces are arranged to reflect UV-C radiation at said object so that the UV-C radiation received by said object is substantially uniform.

35. A process of disinfecting an object as described in claim 19, further comprising the steps of:
   determining a predetermined minimum reference level of UV-C radiation for the object to be disinfected according to the specific pathogen or pathogens to be treated; and
   terminating the emission of UV-C radiation after determining that the required predetermined minimum reference level of UV-C radiation has been received by each of said sensors.

* * * * *